United States Patent [19]

Oppici et al.

[11] Patent Number: 4,656,304

[45] Date of Patent: Apr. 7, 1987

[54] ASPARTAME SYNTHESIS

[75] Inventors: Ernesto Oppici, Milan; Franco Dallatomasina, Segrate; Pietro Giardino, Milan, all of Italy

[73] Assignee: Farmitalia Carlo Erba S.p.A., Milan, Italy

[21] Appl. No.: 614,150

[22] Filed: May 25, 1984

[30] Foreign Application Priority Data

May 31, 1983 [GB] United Kingdom ............... 8314907

[51] Int. Cl.$^4$ ............................................. C07C 101/02
[52] U.S. Cl. .................................................... 560/41
[58] Field of Search ................... 260/112.5 R; 560/41

[56] References Cited

U.S. PATENT DOCUMENTS

| | | | |
|---|---|---|---|
| 3,492,131 | 1/1970 | Schlatter et al. | 260/112.5 |
| 3,833,553 | 9/1974 | Ariyashi et al. | 260/112.5 R |
| 3,962,207 | 6/1976 | Uchiyama et al. | 260/112.5 R |
| 4,071,511 | 1/1978 | Takemoto et al. | 260/112.5 R |
| 4,173,562 | 11/1979 | Bachman et al. | 260/112.5 R |

FOREIGN PATENT DOCUMENTS 0058063 8/1982 European Pat. Off. .

OTHER PUBLICATIONS

Handbook of Chemistry and Physics, 57th ed., CRC Press, Ohio, 1976–1977, p. B–139.

*Primary Examiner*—Donald B. Moyer
*Assistant Examiner*—F. T. Moezie
*Attorney, Agent, or Firm*—Oblon, Fisher, Spivak, McClelland & Maier

[57] ABSTRACT

A process for the preparation of the N-L-α-aspartyl-L-phenylalanine 1-methyl ester (aspartame) which is characterized by adding phosphoric acid and a lower alkyl alcohol to the reaction mixture containing N-formyl α-L-aspartyl- and β-L-aspartyl-L-phenyl-alanine methyl ester and only one of the resultant deformylated isomers, i.e. aspartame phosphate precipitates.

The α-isomer phosphate is collected by filtration and converted to free aspartame by treatment with a base.

6 Claims, No Drawings

ASPARTAME SYNTHESIS

DESCRIPTION

The invention relates to a new synthesis for aspartame, i.e. α-L-aspartyl-L-phenylalanine methyl ester. Aspartame has sweetening properties like cane and beet sugar, and is used as a sweetening agent for foods and beverages as in U.S. Pat. No. 3,492,131.

Aspartame is a dipeptide, and as such is formed with an amide bond between an activated carboxyl group of one amino acid and the amino group of another amino acid. Activation is necessary to increase the rate and the yield of the condensation. The desired pure peptide requires the protection of all other functional groups not involved in the peptide bond formation. Finally, the protecting groups are removed.

Aspartame can be prepared by reaction of N-protected-L-aspartic anhydride with L-phenyl-alanine methyl ester. This gives a mixture of N-protected α-L-aspartyl- and β-L-aspartyl-L-phenylalanine methyl ester which requires the N-deprotection of the compound followed by the separation of the two isomers.

The N-protecting groups are the common N-protecting group used in the peptide chemistry, like benzyloxycarbonyl- and formyl-group. It is very well known that the reaction to remove these N-protecting groups is complicated since the splitting of peptidic bonds takes place at the same time with formation of undesired by-products, such as diketopiperazine.

The N-deprotection reaction carried out according to the known techniques commonly used are performed in the presence of strong acid (U.S. Pat. No. 4,071,511) or in the presence of hydroxylamine (U.S. Pat. No. 4,021,418). Although these processes are considered to be suitable from an industrial point of view, several disadvantages have been pointed out such as low yields, expensive reagents, esterification of β-carboxy group and hydrolysis of ester or peptide bonds. Furthermore, the product so obtained is not pure being mixed with substantial amounts of by-products.

It is necessary, therefore, to subsequently purify the product with the resulting increase of the manufacturing costs.

Furthermore, it is known that a mixture of α- and β-isomers is formed during the process for preparing aspartame and, therefore, a further step for separating the α- and β-isomers is required since the β-isomer does not have sweetening properties. This leads to a further increase of the manufacturing cost.

It has now unexpectedly found a new and very simple process which does not present the above mentioned disadvantages.

THE INVENTION

According to the present invention, there is provided a process for removing the N-formyl group from the L-aspartyl-L-phenylalanine methylester of which the amino group of the aspartyl moiety is protected by the formyl group, which process enables to separate contemporaneously the wished α-isomer from the β-one.

More particularly, the present invention provides a process for preparing aspartame which is characterized by adding phosphoric acid and a lower alkyl alcohol to the reaction mixture containing N-formyl α-L-aspartyl- and β-L-aspartyl-L-phenyl-alanine methyl ester obtained by condensation between N-formyl-L-aspartic anhydride and L-phenylalanine methyl ester. Only one of the resultant deformylated isomer compounds, i.e. α-L-aspartyl-L-phenylalanine methyl ester precipitates as sparingly soluble phosphate.

The spontaneously separated α-isomer phosphate is collected by filtration and converted to free aspartame by treatment with a base.

The removal of the formyl group directly in the condensation mixture avoids the isolation of N-formyl aspartame and reduces production costs.

The industrial process for preparing α-L-aspartyl-L-phenylalanine methyl ester is further on simplified by the present invention: it is not necessary a specific step for separating the wished peptide from the β-isomer formed in the condensation, as only aspartame phosphate crystalizes from the reaction mixture after completation of th deprotection.

The mild acidic hydrolysis of our process prevents the peptide bond from splitting and avoids the remotion the alcohol moiety from the ester or esterification of the free β-carboxyl group.

Lastly, the conditions employed in the present invention avoid formation of the undersired by-product diketopiperazine. With reference to the experimental conditions, the condensation mixture wherein the N-deformylation is directly carried out is formed by an organic solvent and an organic acid, preferably ethylacetate or dichloroethane and acetic acid.

The phosphoric acid which is employed in the method of the present invention may have a percent concentration in water in the range of from 50% to 99%, preferably 85%.

The phosphoric acid to be used is in an amount of from 1.2 to 5 moles per mole of N-formyl aspartame to be deformylated.

As regards the alcohol which is added together with the phosphoric acid to the reaction mixture, it has from one to four carbon atoms and is preferably methyl alcohol. The deformylation is carried out at a temperature of from room temperature to 60° C., for from 4 to 12 hours.

The desired pure compound is collected as its phosphate from the reaction product mixture by cooling the reaction mixture after the completion of the reaction.

The aspartame phosphate thus obtained is converted to free aspartame by neutralizing the phosphate with the use of a base such as sodium carbonate, sodium hydroxyde or ammonia in an aqueous solvent.

The present invention provides a commercially very useful process for preparing aspartame, because, in accordance with the present invention, the desired pure peptide can be produced eliminating two steps, isolation of N-formylaspartame and separation of α- and β-isomers, with isolation yields higher than those achieved in accordance with the conventional prior art processes.

The invention is further illustrated by the following examples.

EXAMPLE 1

To a solution of 100 g of N-formyl-α,β-L-aspartyl-L-phenylalanine methyl ester (α/β-isomer ratio 8:2) in 160 ml of dichloroethane and 40 ml of acetic acid, 360 ml of methyl alcohol and 35.2 ml of 85% aqueous phosphoric acid were added at room temperature.

The mixture was heated at 40° C. for eight hours and then cooled.

The α-L-aspartyl-L-phenylalanine methylester phosphate which crystallized out were collected by filtration and dried.

Yield, 85% (on the basis of the N-formylaspartame).

EXAMPLE 2

51 g of α-L-aspartyl-L-phenylalanine methylester phosphate were dissolved in 300 ml of water. The resulting solution was adjusted to pH to 5.2 with 20% aqueous NaOH stirred for one hour at room temperature, cooled and the precipitated free aspartame collected by filtration.

27.9 g of pure compound were obtained in 73% yield, m.p. 233°–235° C. (dec.), $[\alpha]_D^{22} = +33.2$ (c=1, acetic acid)

EXAMPLE 3

To a solution of 100 g of N-formyl-α,β-L-aspartyl-L-phenylalanine methyl ester (α/β-isomer ratio 8:2) in 380 ml of ethylacetate and 40 ml of acetic acid, 400 ml of methyl alcohol and 70.4 ml of 85% aqueous phosphoric acid were added.

Operating as in example 1, the aspartame phosphate was obtained in 90% yield.

EXAMPLE 4

Operating as in example 1, but using phosphoric acid 99% instead of 85%, the aspartame phosphate was obtained in 75% yield.

EXAMPLE 5

Operating as in example 1, but using aqueous phosphoric acid 50% instead of 85%, the aspartame phosphate was obtained in 65% yield.

We claim:

1. In a process for the purification of N-L-α-aspartyl-L-phenylalanine L-methyl ester, from a mixture of α- and β-isomers obtained by reacting N-protected-L-aspartic anhydride with L-phenylalanine methyl ester in a mixture of either ethyl acetate or dichloroethane and acetic acid, the improvement which comprises treating said dissolved mixture with 85% phosphoric acid and a lower alkyl alcohol, thereby precipitating the sparingly soluble aspartame phosphate, collecting the same by filtration, dissolving the aspartame phosphate in water and subsequently neutralizing the aspartame phosphate with an inorganic base, thereby generating the purified aspartame in a yield of about 73–90% based on the N-protected aspartame, and wherein the amount of phosphoric acid used is from 1.2 to 5 moles per mole of N-protected aspartame to be deformylated, and wherein the reaction is carried out at a temperature from room temperature to 60° C., for a period of from 4 to 12 hours.

2. The process according to claim 1, wherein a volume ratio range of either dichloroethane or ethyl acetate to acetic acid of about 4:1 to 10:1 is used.

3. The process according to claim 1, wherein the lower alkyl alcohol has from 1 to 4 carbon atoms.

4. The process according to claim 3, wherein the lower alkyl alcohol is methyl alcohol.

5. The process according to claim 1, wherein said organic solvent is ethyl acetate or dichloroethane.

6. The process according to claim 1, wherein said inorganic base is an aqueous solution of sodium carbonate, sodium hydroxide or ammonia.

* * * * *